(12) United States Patent
El Gowini et al.

(10) Patent No.: US 9,250,119 B2
(45) Date of Patent: Feb. 2, 2016

(54) APPARATUS AND METHOD FOR CHARACTERIZING ADHESIVE BONDING AND OSSEOINTEGRATION

(71) Applicants: The Governors of the University of Alberta, Edmonton (CA); Alberta Health Services, Edmonton (CA)

(72) Inventors: Mohamed Mahmoud Taher El Gowini, Edmonton (CA); Walied Ahmed Mohamed Moussa, Edmonton (CA); Edmond Hok Ming Lou, Edmonton (CA)

(73) Assignees: The Governors of the University of Alberta, Edmonton (CA); Alberta Health Services, Edmonton (CA)

( * ) Notice: Subject to any disclaimer, the term of this patent is extended or adjusted under 35 U.S.C. 154(b) by 327 days.

(21) Appl. No.: 13/907,748

(22) Filed: May 31, 2013

(65) Prior Publication Data
US 2014/0150558 A1    Jun. 5, 2014

Related U.S. Application Data

(60) Provisional application No. 61/654,229, filed on Jun. 1, 2012.

(51) Int. Cl.
*G01H 11/08* (2006.01)
*G01N 29/24* (2006.01)

(52) U.S. Cl.
CPC ........... *G01H 11/08* (2013.01); *G01N 29/2475* (2013.01); *G01N 2291/0251* (2013.01)

(58) Field of Classification Search
CPC .............................. G01N 29/00; G01H 11/08
USPC ............................................ 73/658; 156/4, 64
See application file for complete search history.

(56) References Cited

U.S. PATENT DOCUMENTS

| 5,587,130 | A | * | 12/1996 | Bao et al. | 422/88 |
| 7,343,805 | B2 | * | 3/2008 | Combi et al. | 73/702 |
| 2003/0021185 | A1 | * | 1/2003 | Toda | 367/15 |
| 2006/0172445 | A1 | * | 8/2006 | Chen et al. | 438/17 |
| 2006/0286288 | A1 | * | 12/2006 | Fisk | 427/2.24 |

FOREIGN PATENT DOCUMENTS

| JP | 2008103913 | * | 5/2008 |
| WO | WO2004062477 | * | 7/2004 |

* cited by examiner

*Primary Examiner* — J M Saint Surin
(74) *Attorney, Agent, or Firm* — Christensen O'Connor Johnson Kindness PLLC

(57) ABSTRACT

An apparatus and method is provided for characterizing adhesive bonding using an acoustic wave MEMS sensor. The sensor can consist of a silicon substrate, a thin aluminum nitride film on top of the substrate and a thin gold film above the aluminum nitride layer. An adhesive layer is added on top of the sensor and the dispersion property of acoustic waves in the layered configuration can be utilized for bonding integrity characterization. A wave dispersion model is developed to study the effect of changing the interface stiffness on the wave dispersion profile and to investigate the sensitivity of different sensor configurations. The results of the model illustrate that the dispersion profile shifts in the direction of decreasing wave velocity as the interface stiffness decreases.

12 Claims, 4 Drawing Sheets

APPARATUS AND METHOD FOR CHARACTERIZING ADHESIVE BONDING AND OSSEOINTEGRATION

CROSS-REFERENCE TO RELATED APPLICATIONS

This application claims priority of U.S. Provisional Patent Application Ser. No. 61/654,229 filed Jun. 1, 2012, and hereby incorporates the same provisional application by reference herein in its entirety.

TECHNICAL FIELD

The present disclosure is related to the field of apparatuses and methods for characterizing adhesive bonding. In particular, the present disclosure is related to the field of acoustic wave micro-electro-mechanical systems ("MEMS") sensors for characterizing adhesive bonding and osseointegration of man-made implants in a human body.

BACKGROUND

Adhesives are widely used bonding materials that offer lightweight, high strength load bearing structures and can be used with a wide range of adherend materials such as metals, plastics, rubbers, composites and wood. Adhesives' applications can include bone repair procedures in orthopedics, bonded patch applications in airplanes, electronics packaging and building materials. Monitoring the quality of an adhesive bond is an essential procedure to ensure the safety of components in service. There are various mechanisms that lead to adhesive bonding degradation; such as moisture absorption, cracks, inclusions, wear, poor cure, and porosity. Numerous techniques exist for monitoring the quality of an adhesive bond, such as acoustic emission [1,2], radiography testing [3] and ultrasonic techniques. Ultrasonic techniques include normal and/or oblique incidence [4,5] and guided wave techniques, [6,7]. Guided wave techniques offer advantages such as confinement of the wave energy near the adhesive-adherend interface, which makes the wave highly sensitive to the interfacial mechanical properties and bonding conditions. In addition, guided waves propagate along the interface and can inspect large components much faster than with normal/oblique incidence methods.

Surgical implants play a major role in the lives of many people who experience serious injuries. Implants are man made devices that are "implanted" in the human body to replace, support and/or enhance biological components or structures in the body. Different kinds of implants can be inserted in the human body, which include knee, dental, hip and craniofacial implants such as nose, ear and eye. An important bonding process initiates at the prosthetic implant's surface after insertion. The bone tissue develops to form a strong bond with the implant surface (usually Titanium Oxide) and prevents relative motion. This process is called osseointegration and is an indicator of healing progression. Osseointegration was discovered by Brânemark in the 1950's, when he realized that rabbit bone could be permanently attached to titanium implants. It is defined as the formation of a direct contact between living bone and implant. This process allows the permanent fixation of the implant to the surrounding bone tissue. While osseointegration occurs with various types of prostheses focus will be on osseointegration of hip implants.

Total hip replacement ("THR") is a surgical procedure adopted to replace a dysfunctional hip joint assembly. This procedure helps to a great extent to restore normal gait conditions to the patient and alleviate the pain due to a failed hip joint assembly. The hip joint consists of the femoral head, which is attached to the acetabulum to form a ball and socket arrangement. Deterioration of the hip joint could be caused by arthritis, which occurs with age due to degeneration of the articular cartilage. The wear of the articular cartilage causes bone to grind against bone; this causes severe pain, inhibits motion and eventually leads to bone fracture. Another cause is the significant reduction in bone density that leads to bone fracture and damage of the blood vessels. A common cause of hip joint deterioration among the young generation is injury due to extreme exercise.

The THR procedure is an intensive procedure, where the patient has to be completely sedated. The purpose of the operation is to replace a damaged hip joint assembly with a prosthetic implant. There are two commonly used approaches to ensure the formation of a strong bond between the implant surface and the bone. Either to use bone cement to enhance implant fixation i.e. cemented implant, or to use an un-cemented implant. In the latter case, the implant surface is coated with a porous layer to stimulate bone growth and the formation of a strong bond.

Post surgical complications are very common in THR procedures and patient follow-up is crucial. The most common type of complication is implant loosening, which occurs due to the bone re-modeling process that takes place after implant insertion. Remodeling takes place due to the changes in the loads transferred to the bone as a result of inserting an implant with a significantly different stiffness, which therefore shields the bone from the stresses normally transferred. This process leads to loss of bone mass and reduced bone density, which ultimately leads to implant loosening.

The bones in the wrists and ankles are considered to be short bones, while bones in the arms and legs, such as the femur are considered to be long bone. Bone is a complex structure. On the macroscopic scale it consists of two main layers; cortical and cancellous. Cortical bone is the compact outer layer that acts as a protective layer. Cancellous bone is the inner softer layer, which exists mainly in the end of long bone and within vertebrae. It is a porous structure formed of trabecular tissue. Although the cancellous bone is a soft tissue, the individual trabeculae are much stiffer than the bulk.

A wide range of values for the elastic modulus of single trabeculae have been determined. This variability is due to the differences and limitations in measurement techniques. The range of elastic modulus for single trabeculae is 1-20 GPa and the density is in the range of 1,600-2,600 kg/m$^3$. The size of single trabeculae is in the range of 100-500 μm. On the other hand, the stiffness of the cancellous bone is lower than for single trabeculae. The range of values for the elastic modulus is 10-4,000 MPa and the density is 150-1,000 kg/m$^3$. The elastic modulus is related to the apparent density (density of the trabecular structure and pores) through an empirically determined power law.

Various mechanisms exist for detecting osseointegration of hip implants. Imaging techniques such as X-Ray imaging, Dual Energy X-Ray Absorptiometry ("DEXA") and Quantitative Computed Tomography ("q-CT") are commonly used. Plain radiographs are widely used but have been shown to be highly inaccurate. It has been shown that unless a significant level of bone mineral density occurs; up to 70%, radiological signs will not be conclusive. DEXA, on the other hand, can provide a quantitative assessment of the bone mineral density; however, some unreliability exists since it depends on the exact positioning of the patients and errors would be introduced by patient movements. Quantitative CT-scans are widely used since they provide an accurate quantitative assessment of the bone mineral content; however its major drawback is the high radiation exposure.

Another approach is using vibration techniques. This approach can use sound waves in the audio range to excite femoral hip-implant assembly in vitro at different stages of cement curing. The results indicated that there was indeed an upward shift in the frequency response of the entire assembly. This approach has also been used to demonstrate that there is a shift in the natural frequency measurements of femurs with fixed and loose prostheses. Clinical studies have found that when loosening of the implant occurs, it can be detected by changes in the output signal. However, in an attempt to detect early stages of implant loosening, a study conducted on cadaver femora by simulating different stages of implant loosening and exciting the system with a sinusoidal force indicated that the system was performing well in detecting late stages of implant loosening but failed to identify early stages of implant loosening.

Further studies have investigated the accuracy of vibration detection techniques. Results were collected from vibration tests on a group of patients, as well as x-ray data for the same patients and were compared with each other. The results concluded that vibration testing was 20% more sensitive and diagnosed 13% more patients when compared with x-ray data.

A new generation of bio-implantable sensors is gaining momentum due to the major advances in the field of Micro-electro-mechanical Systems (MEMS). Implanting miniature sensors in the human body can be a major achievement. This would allow surgeons to monitor all parameters of interest in-vivo, which would lead to more tailored prescriptions, accurate assessments and early prediction of possible complications. In essence, each patient could become a biomechanics laboratory.

Various researchers have utilized bio-implantable MEMS sensors for in-vivo analyses. One has investigated the biocompatibility and wound healing behavior of bone tissue due to implanting a piezoresistive MEMS sensor in an animal spine. Results indicated healthy bone remodeling and no signs of inflammation or bone abnormalities. Another discussed the possibilities of using MEMS sensors in the spine and femur to measure fluid pressure.

The potential of bio-implantable sensors was also extended to the problem of implant loosening. Piezoresistive MEMS sensors have been utilized to measure the stresses at the bone implant interface in hip and knee implants respectively. Both approaches infer healing progression from the stress measurements since it is expected that the loads measured by the sensor will increase as healing progresses. In these approaches, values were assumed for the bone properties and the stresses were calculated accordingly.

It is, therefore, desirable, to provide an apparatus and method for characterizing adhesive bonding and osseointegration that overcomes the shortcomings in the prior art.

SUMMARY

An apparatus and method for characterizing adhesive bonding is provided. In some embodiments, the apparatus and method can allow monitoring of osseointegration of a man-made implant inserted into a human body and predict whether implant loosening would occur. In so doing, the apparatus and method can alleviate the severe pain suffered by patients due to implant loosening and prevent having to do re-correction surgeries. While this disclosure discusses apparatuses and methods for characterizing adhesive bonding and osseointegration of man-made implants for insertion in human bodies, it is obvious to those skilled in the art that the apparatuses and methods described herein can be adapted and configured to characterize adhesive bonding between two surfaces or materials in general, and are not limited to characterizing adhesive bonding and osseointegration of man-made implants.

In some embodiments, the apparatus and method can predict implant loosening directly by monitoring two properties at the interface between the implant and the bone: a) the stiffness of the bone layer; and b) the stiffness of the interface wherein the implant comprises an acoustic wave MEMS sensor disposed therein. In other embodiments, the apparatus and method can allow healthcare providers to identify the location where loosening of the implant is occurring.

In some embodiments, the apparatus and method can: a) characterize the curing process of an interfacial layer; b) characterize the change in stiffness of the adjacent bone layer; c) characterize the change in stiffness of the interface in the location of the sensor; d) allow healthcare providers to predict early stages of implant loosening; and e) allows healthcare providers to determine where implant loosening is occurring.

Incorporated by reference into this application in its entirety is a paper written by the within inventors entitled, "ADHESIVE BONDING CHARACTERIZATION USING AN ACOUSTIC WAVE MEMS SENSOR", submitted for publication in the Proceedings of the $23^{rd}$ CANCAM 2011 conference held in Vancouver, British Columbia, Canada on Jun. 5-9, 2011. All of the reference documents listed in this paper are also incorporated by reference into this application in their entirety.

Broadly stated, in some embodiments, an acoustic wave sensor is provided, comprising: a semiconductor substrate; a piezoelectric layer disposed on the substrate; a metallic layer disposed on the piezoelectric layer; and an input electrode and an output electrode disposed on the substrate, the electrodes disposed between the substrate and the piezoelectric layer.

Broadly stated, in some embodiments, an apparatus is provided for characterizing adhesive bonding, comprising an acoustic wave sensor comprising: a semiconductor substrate; a piezoelectric layer disposed on the substrate; a metallic layer disposed on the piezoelectric layer; and an input electrode and an output electrode disposed on the substrate, the electrodes disposed between the substrate and the piezoelectric layer.

Broadly stated, in some embodiments, a method is provided for characterizing adhesive bonding, the method comprising the steps of: providing an acoustic wave sensor, comprising: a semiconductor substrate, a piezoelectric layer disposed on the substrate, a metallic layer disposed on the piezoelectric layer, and an input electrode and an output electrode disposed on the substrate, the electrodes disposed between the substrate and the piezoelectric layer; placing the sensor between two surfaces or two materials to be adhered together; placing an adhesive layer between the two surfaces or two materials wherein an adhesive bond is formed between the two surfaces or two materials; exciting the sensor wherein the sensor generates acoustic waves wherein the acoustic waves propagate through the sensor and the adhesive layer; and monitoring the acoustic waves; and determining the strength of the adhesive bond from the monitored acoustic waves.

DETAILED DESCRIPTION OF EMBODIMENTS

Figure 1:
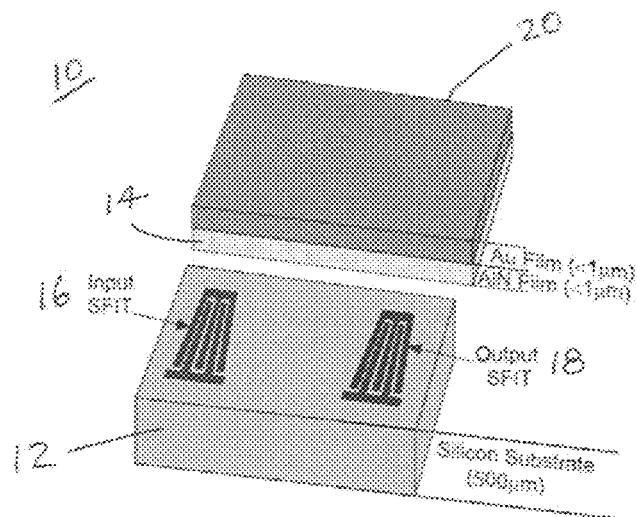
FIG. 1 is a perspective view depicting one embodiment of an acoustic wave sensor comprising slanted finger interdigital ("SFIT") electrodes.

An apparatus and method is provided utilizing an acoustic wave sensor for characterizing adhesive bonding integrity and osseointegration. One embodiment of acoustic wave sensor 10 is illustrated in FIG. 1. In some embodiments, sensor 10 can comprise of silicon ("Si") (100) substrate 12, aluminum nitride ("AlN") film 14 deposited on the surface of Si substrate 12, two sets of electrodes 16 and 18 (input and output, respectively) patterned at the AlN—Si interface and thin gold ("Au") film 20 deposited on the surface of AlN film 14. AlN film 14 is piezoelectric and can allow electrical excitation of acoustic waves.

In some embodiments, AlN and Au films 14 and 20 can be guiding layers and can confine the wave near the interface, which can increase its sensitivity to changes in the adjacent environment. A wide band acoustic wave signal can be generated using the Slanted Finger Interdigital ("SFIT") electrode configuration as illustrated in electrodes 16 and 18 in FIG. 1. In the slanted geometry the electrode period (distance between two similarly charged electrode fingers) can vary linearly along the length of the fingers. The narrow periods can excite higher frequency waves, while the wider periods can excite lower frequency waves. The wide band acoustic signal can facilitate generation of a wave dispersion profile.

In some embodiments, there can be a number of features that an acoustic wave MEMS sensor can provide for adhesive bonding characterization that can include quantification of interfacial imperfections and degradation in bonding strength, which can be related directly to the wave dispersion characteristics. The reduced size of the sensor can allow it to be embedded along the adhesive-adherend interface to provide a localized diagnosis of interface properties. In addition, the proposed sensor configuration can facilitate the propagation of an interface wave that can be highly sensitive to interfacial properties.

In some embodiments, a wave dispersion model is provided that can generate a dispersion profile of a wave propagating in the multi-layered configuration and monitor the shift in the wave dispersion profile due to adhesive bonding degradation. Using this information, the sensitivity of different sensor configurations can be examined to select the configuration with highest sensitivity for device fabrication.

Wave Dispersion Model

A. Generating the Au—AlN—Si Dispersion Curve

In order to be able to generate the dispersion profile for a multi-layered configuration, it is essential to solve the wave equation in each layer. The Au and AlN films on top of the silicon substrate can act as guiding layers and their thicknesses comprise characteristic dimensions that can lead to wave dispersion. The wave equation can be written as:

$$[\Gamma_{pq} - \delta_{pq}\rho v^2][\alpha_p] = 0 \qquad (1)$$

$$|\Gamma_{pq} - \delta_{pq}\rho v^2| = 0 \qquad (2)$$

where $\gamma_{pq}$ refers to the Christoffel stiffness constants, which are functions of the material properties and the decay parameter b. The subscripts p and q can have the values 1, 3 and 4, which correspond to the displacement components $u_1$, $u_3$ and the electric potential $\phi$, respectively; $\delta_{pq}$ is the Kronecker delta function, $\rho$ is the density of the medium in kg/m³, v is the phase velocity in m/s, $\alpha_p$ is the relative wave amplitude vector. Mason [8] provides a detailed derivation of the Christoffel equation and the expressions for the Christoffel constants. By solving the secular equation (2) for a given phase velocity v, the decay parameter b and the relative wave amplitude vector $\alpha_p$ can be determined. The plane wave solutions for a given medium in the sagittal plane ($x_1$-$x_3$) can be written as a summation of partial wave solution as follows:

$$u_j = \sum_n C_n \alpha_j^n \exp(ikb^n x_3)\exp[ik(x_1 - vt)]; \quad j=1,3 \qquad (3)$$

$$\phi = \sum_n C_n \alpha_4^n \exp(ikb^n x_3)\exp[ik(x_1 - vt)] \qquad (4)$$

where k is the wave number and the $C_n$ are weighting factors. In the piezoelectric AlN film the wave solutions are the coupled mechanical displacements $u_j$ and the electric potential $\phi$ given in (3) and (4), respectively. For the Au film and Si substrate, which are non-piezoelectric, the potential and the displacement solutions can be de-coupled.

In some embodiments, when the wave solutions for each medium are generated, it is essential to find the value of the phase velocity that sets the determinant of the boundary condition matrix to zero. The dispersion profile can then be obtained by finding the velocity values that satisfy the boundary condition matrix at different frequencies.

Figure 2:
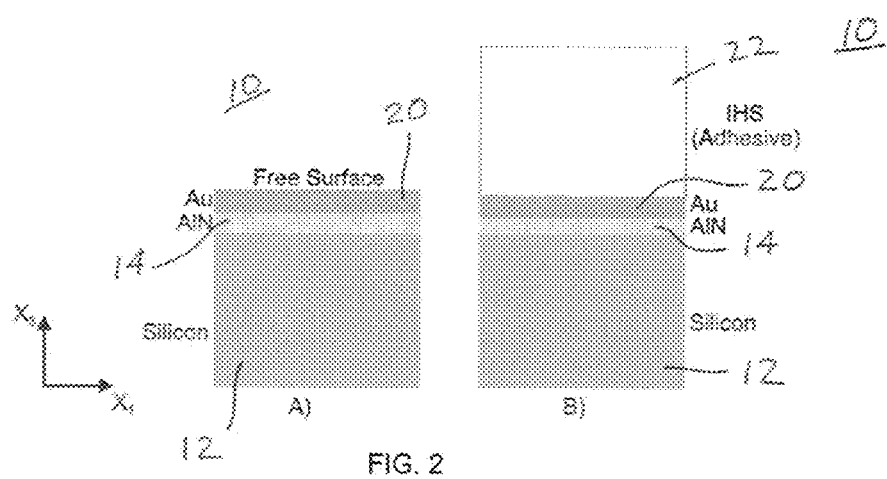
FIG. 2a) is a cross-section view depicting an Au—AlN—Si (no-bond) configuration.
FIG. 2b) is a cross-section view depicting an IHS—Au—AlN—Si (perfect-bond) configuration.

A schematic of the three layer configuration (Au—AlN—Si) of sensor 10 is shown in FIG. 2a). This configuration is referred to in this disclosure as the no-bond case because the top surface of Au film 20 is a free surface.

Figure 3:
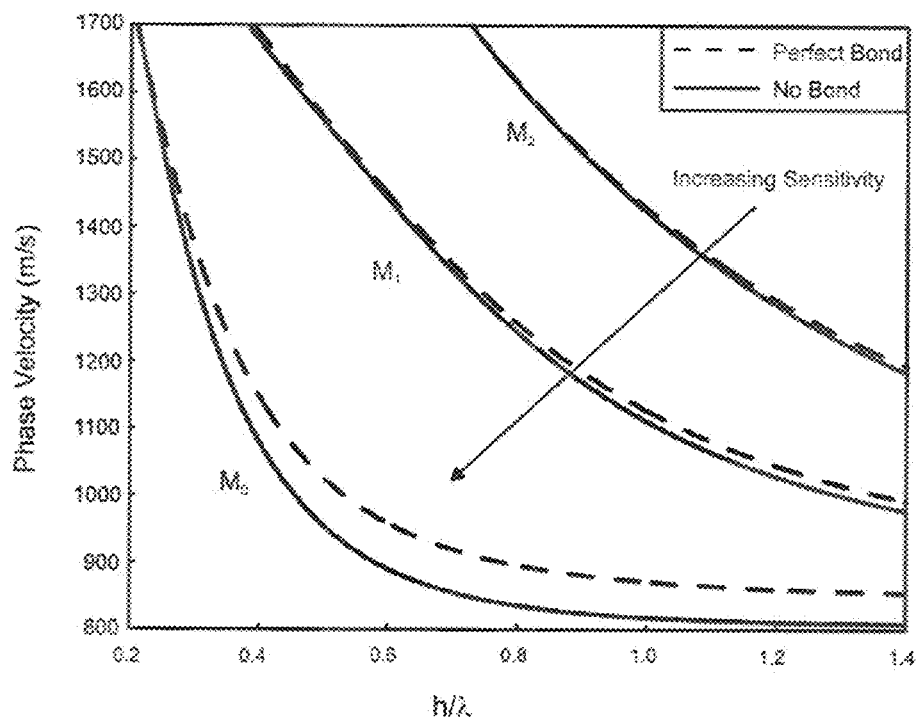
FIG. 3 is an X-Y graph depicting dispersion profiles of the first three modes of wave propagation in the no-bond and perfect-bond cases.

To study the effect of changing interface properties on the wave dispersion profile, adhesive layer 22 can be added on top of sensor 10 as illustrated in FIG. 2b). The wave solutions in adhesive layer 22 can be taken into account in addition to the boundary conditions at the adhesive-gold interface. Adhesives can have numerous applications and their material properties can vary significantly, the elastic modulus of structural adhesives can be as high as 10 GPa [9]. Adhesive layer 22 can be modeled as an isotropic half space ("HIS") with an elastic modulus of 8 GPa and it is assumed to be perfectly bonded to Au film 20, that is, continuity of displacement and stresses in the sagittal plane. This configuration is referred to as the perfect-bond case in this disclosure. The dispersion profiles showing the first three modes of wave propagation for the no-bond and perfect-bond cases are shown in FIG. 3.

The dispersion curves illustrate the variation in wave velocity with the dimensionless parameter $h/\lambda$. The parameter h refers to the thicknesses of the Au and AlN films, and $\lambda$ refers to the distance between two similarly charged electrode fingers. As the value of $h/\lambda$ increases, the wave can be more confined near the interface and can propagate with a higher frequency.

B. Spring Boundary Model

Figure 4:
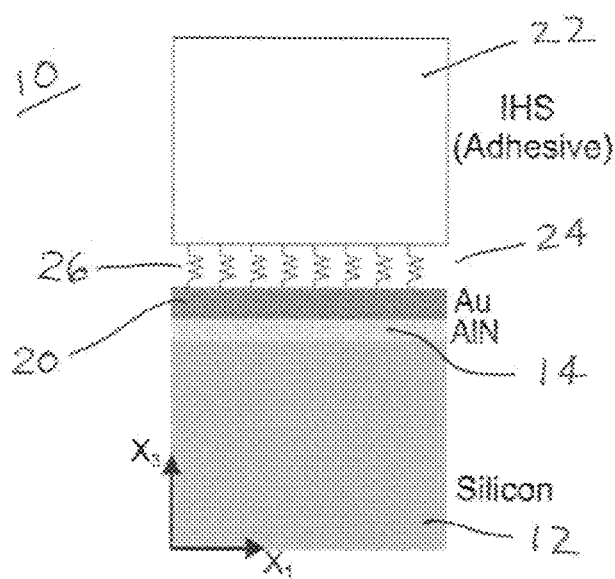
FIG. 4 is a cross-section view depicting a four-layer configuration (IHS—Au—AlN—Si) with a spring boundary at the IHS—Au interface.

In some embodiments, interfacial imperfections along the adhesive bond line can often be confined to a very thin layer near the interface. The overall effect of these imperfections can reduce the interface stiffness, which can lead to an increase in the far-field displacement at a given load as a result of bond degradation. To account for the reduction in interface stiffness at the adhesive bond line, the interface can be modeled as a layer of distributed mass-less springs with spring stiffness K (N/m$^3$). This is known as the spring boundary model, and has been frequently used to study the effect of interface imperfections on wave propagation characteristics [10-12]. FIG. 4 shows a schematic of the IHS—Au—AlN—Si configuration with spring boundary 24 at the IHS—Au interface.

When a load is applied, interfacial springs 26 can be distorted leading to a discontinuous displacement field across the interface. The stresses, on the other hand, can be continuous across the interface to keep the layers intact and can be proportional to the discontinuous displacement field.

The boundary conditions for the IHS—Au—AlN—Si configuration with spring boundary 24 are shown in Table 1 as shown below:

TABLE 1

Boundary Conditions for the Different Interface Conditions

| Boundary Conditions | AlN—Si | AlN—Au | Au-IHS |
|---|---|---|---|
| $u_3 = u_3'$ | ✓ | ✓ | |
| $u_1 = u_1'$ | ✓ | ✓ | |
| $T_{13} = T_{13}'$ | ✓ | ✓ | |
| $T_{33} = T_{33}'$ | ✓ | ✓ | |
| $D_3 = D_3'$ | ✓ | ✓ | |
| $\phi = \phi'$ | ✓ | | |
| $\phi = 0$ | | ✓ | |
| $T_{33} = T_{33}' = K[u_3' - u_3]$ | | | ✓ |
| $T_{13} = T_{13}' = K[u_1' - u_1]$ | | | ✓ | where $u_1$ and $u_3$ refer to the displacements (m) in the 1 and 3 directions, respectively. $T_{13}$ and $T_{33}$ refer to the normal and shear stresses (N/m$^2$) in the sagittal plane, respectively. $D_3$ is the electric displacement component (C/m$^2$). $\phi$ is the electric potential (V). K is the interface stiffness (N/m$^3$). There are three interfaces in this configuration (AlN—Si, AlN—Au and Au—IHS), which are listed in the top row of Table 1. When a boundary condition is applied at an interface, the interface is marked with (✓).

Results

Figure 5:
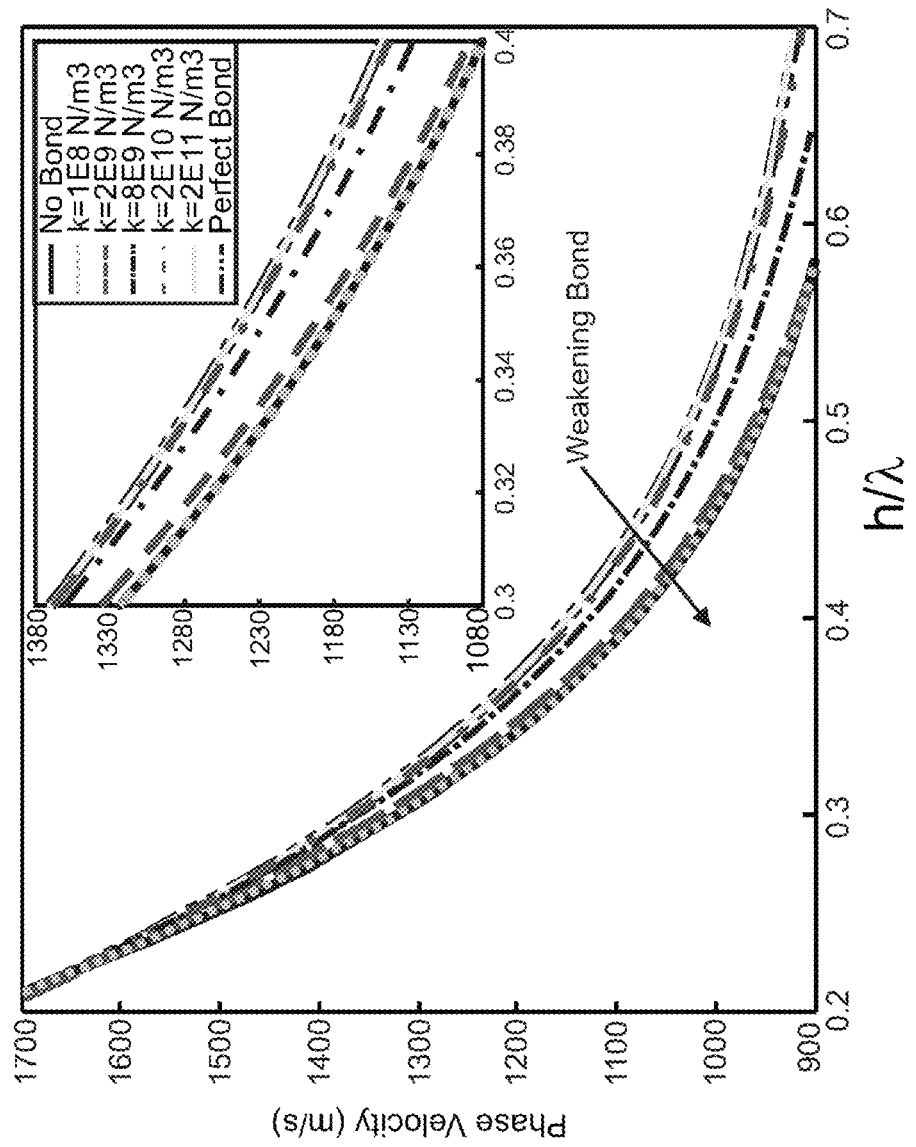
FIG. 5 is an X-Y graph depicting the shift in the wave dispersion profile of the $M_0$ mode of the HIS—Au—AlN—Si configuration due to changing interface stiffness (K).

The effect of changing the interface stiffness on the fundamental mode ($M_0$) of the wave dispersion profile of the IHS—Au—AlN—Si configuration shown in FIG. 3 can be investigated using the wave dispersion model. The shift in the fundamental mode of the dispersion profile at different interface stiffness values is shown in FIG. 5. The inset provides a better illustration of the shift in the dispersion profile.

Figure 6:
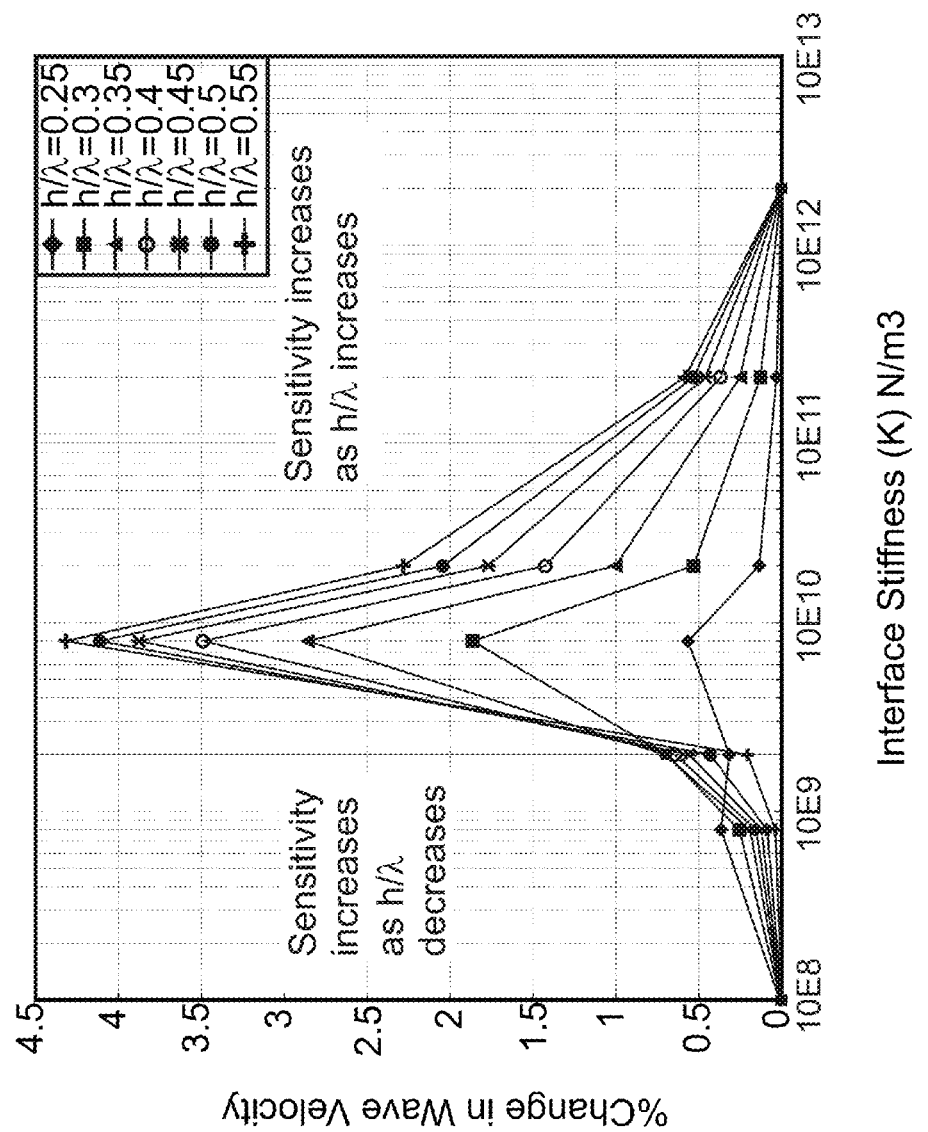
FIG. 6 is an X-Y graph depicting the percentage increase in wave velocity (%) for different $h/\lambda$ configurations as the interface stiffness increases.

The results in FIG. 5 can provide sufficient information to calculate the change in wave velocity at various interface stiffness values to examine the sensitivity of the different h/λ configurations. FIG. 6 illustrates the change in wave velocity (%) as the interface stiffness changes from the no bond case to the perfect bond case.

DISCUSSION

The effect of adhesive bonding degradation has been investigated using the shift in the fundamental mode of the wave dispersion profile of the interface wave generated in the multi-layered configuration. In some embodiments, it was found that when the interface stiffness K=2×10$^{11}$ N/m$^3$, the dispersion profile can matche that of the "perfect bond" case, and when K=1×10$^8$ N/m$^3$, the dispersion profile can match that of the "no bond" configuration. FIG. 5 shows the shift in the $M_0$ mode of the wave dispersion profile as the interface stiffness values are reduced. The results indicate that for a given h/λ configuration as the interface stiffness decreases, the wave velocity can also decrease until it reaches that of the no-bond case. Using the shift in the wave dispersion profiles, the sensitivity of different sensor configurations has been investigated.

FIG. 6 illustrates the change in wave velocity as the interface stiffness values change from K=1×10$^8$ N/m$^3$ to K=2×10$^{12}$ N/m$^3$. The results indicate that at K=1×10$^8$ N/m$^3$, the change in wave velocity can be almost negligible for all configurations since this interface stiffness value is equivalent to the "no-bond" case. At the low stiffness values where K=8×10$^8$ N/m$^3$, the low h/λ configurations can have the highest sensitivity. This trend also occurs at K=2×10$^9$ N/m$^3$ except that the sensitivity of h/λ=0.25 drops. This behaviour occurs because up to K=2×10$^9$ N/m$^3$, the interface stiffness is weak and at a given stress level, the interface discontinuity can be high. At low h/λ values, the wave penetrates deeper; therefore, the wave can be more sensitive to the larger displacement discontinuities at the interface. As the interface stiffness reaches K=8×10$^9$ N/m$^3$ and continues to increase, the displacement discontinuity can decrease due to the increased interfacial stiffness. In these cases, the sensitivity can increase with increasing h/λ values because the wave can become more confined near the interface and, therefore, more sensitive to changes in interface stiffness K. In some embodiments, the interface stiffness value was increased to K=2×10$^{12}$ N/m$^3$ and it was found that the change in wave velocity was negligible. This is because K=2×10$^{11}$ N/m$^3$ can be equivalent to the "perfect bond" case, and any further increase in interface stiffness can lead to negligible changes in wave velocity.

From the results in FIG. 6, the range of h/λ=0.3-0.4 appears to be appropriate for designing the sensor due to its high sensitivity throughout the entire range. Configurations with higher h/λ values can have low sensitivity up to K=2×10$^9$ N/m$^3$ and could require higher precision during electrode fabrication and a higher operating frequency range.

CONCLUSION

A new approach for monitoring adhesive bonding degradation using an acoustic wave MEMS sensor has been provided herein. In some embodiments, the approach can be based on examining the shift in the wave dispersion profile due to changing interface stiffness. A wave dispersion model has been developed and can be used to study the effect of changing the interface stiffness on the wave dispersion profile. The results show that as the interface stiffness decreases, there can be a reduction in the wave velocity. In addition, the sensitivity of different sensor configurations has been investigated and the results indicate that the range of h/λ=0.3-0.4 appears to be a choice for sensor fabrication in some embodiments.

In some embodiments, an array of acoustic wave MEMS sensors can be assembled comprising wireless communication means, such as Wi-Fi, Bluetooth or any other functionally equivalent means as well known to those skilled in the art, with an antenna and a power supply that can be attached to an implant before being insertion into a femur during a hip replacement procedure.

Although a few embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

REFERENCES

The following documents are incorporated into this application by reference in their entirety.
[1]. Santulli C, Lucia A C. Relation between Acoustic Emission Analysis during Cure Cycle and Bonded Joint Performances. NDT&E International 1999; 32:333-41.
[2]. Choi N S, Gu J U, Arakawa K. Acoustic Emission Characterization of the Marginal Disintegration of Dental Composite Restoration Composites: Part A 2011; 42(6):604-11.
[3]. Nagarkar V V, Miller S T, Tipnis S V, Gaysinskiy V, Lempicki A, Brecher C. A high-resolution, high-speed CT/radiography system for NDT of adhesive bonded composites. Proceedings of SPIE—The International Society for Optical Engineering 2001; 4503:265-73.
[4]. Brotherhood C J, Drinkwater B W, Dixon S. The Detectability of Kissing Bonds in Adhesive Joints using Ultrasonic Techniques. Ultrasonics 2003; 41(7):521-9.
[5]. Drinkwater B, Dwyer-Joyce R, Cawley P. A Study of the Transmission of Ultrasound Across Solid-Rubber Interfaces. Journal of the Acoustical Society of America 1997; 101(2):970-81.
[6]. Huo S, Reis H. Estimation of Adhesive Bond Strength in Laminated Safety Glass using Guided Mechanical Waves. Proceedings of SPIE—The International Society for Optical Engineering 2007; 6529 PART 1:65290B.
[7]. Le Crom B, Castaings M. Shear Horizontal Guided Wave Modes to Infer the Shear Stiffness of the Adhesive Bond layers Journal of the Acoustical Society of America 2010; 127(4):2220-30.
[8]. Farnell G W, Adler E L. Physical Acoustics Principles and Methods. New York: Academic Press; 1972.
[9]. He X, Oyadiji S O. Influence of Adhesive Characteristics on the Transverse Free Vibration of Single Lap-Jointed Cantilevered Beams. Journal of Materials Processing Technology 2001; 119:366-73.
[10]. Huo S. Estimation of Adhesive Bond Strength in Laminated Safety Glass using Guided Mechanical Waves [PhD thesis]. University of Illinois—Urbana Champaign; 1997.
[11]. Dwyer-Joyce R S, Drinkwater B W, Quinn A M. The Use of Ultrasound in the Investigation of Rough Surface Interfaces. Journal of Tribology 2001; 123(1):8-16.
[12]. Cantrell J H. Determination of Absolute Bond Strength from Hydroxyl Groups at Oxidized Aluminum-Epoxy Interfaces by Angle Beam Ultrasonic Spectroscopy. Journal of Applied Physics 2004; 96(7):3775-81.

We claim:
1. An apparatus for characterizing adhesive bonding, the apparatus comprising an acoustic wave sensor, the sensor comprising:
a semiconductor substrate;
a piezoelectric layer disposed on the substrate;
a metallic layer disposed on the piezoelectric layer; and
an input electrode and an output electrode disposed on the substrate, the electrodes disposed between the substrate and the piezoelectric layer;
wherein the apparatus is configured for characterizing osseointegration of a man-man implant configured for insertion in a human body.
2. The apparatus as set forth in claim 1, further comprising the man-made implant wherein the apparatus is disposed in the man-made implant.
3. A method for characterizing adhesive bonding, the method comprising the steps of:
providing an acoustic wave sensor, comprising:
a semiconductor substrate,
a piezoelectric layer disposed on the substrate,
a metallic layer disposed on the piezoelectric layer, and
an input electrode and an output electrode disposed on the substrate, the electrodes disposed between the substrate and the piezoelectric layer;
placing the sensor between two surfaces or two materials to be adhered together;
placing an adhesive layer between the two surfaces or two materials wherein an adhesive bond is formed between the two surfaces or two materials;
exciting the sensor wherein the sensor generates acoustic waves wherein the acoustic waves propagate through the sensor and the adhesive layer;
monitoring the acoustic waves; and
determining the strength of the adhesive bond from the monitored acoustic waves.
4. The method as set forth in claim 3, wherein the substrate comprises a silicon substrate.
5. The method as set forth in claim 3, wherein the piezoelectric layer comprises an aluminum-nitride film.
6. The method as set forth in claim 5, wherein the aluminum-nitride film is configured to electrically excite acoustic waves.
7. The method as set forth in claim 3, wherein the metallic layer comprises a gold film.
8. The method as set forth in claim 3, wherein one or both of the electrodes comprises a slanted finger interdigital configuration.
9. The method as set forth in claim 3, further comprising disposing an adhesive layer disposed on the metallic layer.
10. The method as set forth in claim 9, wherein the adhesive layer is configured to adhere to a bone.
11. The method as set forth in claim 3, wherein the sensor is configured for characterizing osseointegration of a man-man implant configured for insertion in a human body.
12. The method as set forth in claim 11, further comprising disposing the sensor in the man-made implant.

* * * * *